United States Patent [19]
Chuprikov et al.

[11] Patent Number: 5,137,018
[45] Date of Patent: Aug. 11, 1992

[54] METHOD FOR TREATING THE EMOTIONAL CONDITION OF AN INDIVIDUAL

[76] Inventors: Anatoly P. Chuprikov, 16 linia, 23a, kv. 33., Voroshilovgrad; Igor A. Martsenkovsky, Leninsky prospekt, 14, kv. 48., Donetsk; Mikhail J. Busurin, ulitsa Universitetskaya, 59, kv. 5., Donetsk; Viktor A. Lekakh, prospekt Grinkevicha, 7, kv. 44., Donetsk; Stanislav J. Savitsky, bulvar Shevchenko, 18, kv. 43., Donetsk, all of U.S.S.R.

[21] Appl. No.: 474,445

[22] Filed: Feb. 1, 1990

[51] Int. Cl.$^5$ .............................................. A61N 5/00
[52] U.S. Cl. .................................... 128/395; 600/27
[58] Field of Search ............................. 128/395–398; 600/27

[56] References Cited
U.S. PATENT DOCUMENTS

| | | | |
|---|---|---|---|
| 4,858,609 | 8/1989 | Cole | 600/27 |
| 4,892,106 | 1/1990 | Gleeson, III | 128/395 |

FOREIGN PATENT DOCUMENTS

3447105  7/1985  Fed. Rep. of Germany ........ 600/27

Primary Examiner—Theatrice Brown
Assistant Examiner—Mark S. Graham
Attorney, Agent, or Firm—Burgess, Ryan & Wayne

[57] ABSTRACT

The invention resides in acting simultaneously upon righthand and lefthand halves of the retinas of each eye with two light fluxes at different wavelengths formed of an optical radiation produced by a light source by means of two areas of at least one light filter separated by a boundary. The treatment action is applied at least once until the subjective sensation of a difference in colors disappears.

4 Claims, 5 Drawing Sheets

METHOD FOR TREATING THE EMOTIONAL CONDITION OF AN INDIVIDUAL

FIELD OF THE ART

The invention relates to the medicine, and more particularly, it deals with the physiotherapy and is specifically concerned with methods and apparatuses for correcting the emotional condition of an individual.

The invention may be used in the psychiatry and narcology for treating patients with cyclotomy, seasonal affective disorders, schizophrenia, neuroses, alcoholism; in the sexopathology; for treating emotional disorders in patients with borderline neuro-psychic disorders and also for practically healthy people who are involved in an emotionally intensive activity such as operators, sportsmen, pedagogues; in treating individuals with psychosomatic disorders.

BACKGROUND OF THE INVENTION

Some terms will be defined herein for a better understanding of the invention.

The treatment of the emotional condition here means actions aimed at changing the emotional condition of an individual, in particular, any curative steps. A sagittal plane of the eye is the plane in which the optic axis of the eye is situated which divides the eye lengthwise into the righthand and lefthand halves.

Chemical therapeutical drugs are now used for the treatment of the emotional condition of an individual which are prescribed mainly taking into account the modality and intensity of affective manifestations and, to a much lower degree, taking into account their structure and neurobiological organization (G. Ya. Avrutsky et al. Manual of Physicians. 1981. Meditsina Publishers. Moscow. p.496).

It is known that pathomorphism of the clinical picture of effective disorders occurs at present which, apart from the influence of various social and cultural factors, is the consequence of a wide use of a large number of tranquilizers and antidepressants both in the practice of outpatient clinics and as self-treatment (G. Ya. Avrutsky et al. Pharmacotherapy of Psychic Diseases. 1974. Meditsina Publishers. Moscow. p.154). The same authors believe that a wide use of psychotropic drugs in view of a weakening vitality of endogenic depressions, a decrease in their deepness and transformation of typical phases into superficial forms provides conditions for the appearance of indistinct and superficial depressions resistant to psychopharmacotherapy.

The reduction of the duration of a "fit" of depression under the effect of antidepressants results in a shorter term of remission so that not unfrequently the overall duration of a sickly condition (with a periodical occurrence of a psychosis) remains the same as it was before treatment with antidepressants. In other cases a more easy occurrence of a fit under the favourable effect of antidepressants may result in a more prolonged course of the disease (P. V. Birjukovich et al. Pharmacological Fundamentals of the Antidepressive Effect. 1970. Leningrad. pp. 61-65; P. V. Birjukovich et al. Circular Depression. 1979. Naukova Dumka Publishers. Kiev. p. 324).

Known in the art are methods for treating affective disorders which make it possible to take into account structure and neurobiological organization of the affective disorders. Such methods include methods of lateral physiotherapy carried out by acting with stimuli of various modality and intensity selectively upon the right and left hemispheres of the brain depending on prevalence of manifestations of the right or left hemispherical disorders (N. I. Bragina et al. Functional Asymmetries in a Human Being. 1988. Meditsina Publishers. Moscow. pp. 195-203).

Known in the art is a method for treating depressions (SU, A, 725671), comprising, in order to cut down prolonged and hardly curable depressions, examining the sensory excitability of the hands and acting with electric pulses with a voltage 2-3 times as low as the sensitivity threshold and with a pulse repetition rate from 10 to 100 Hz. The electrodes are applied to one hand: the anode being applied to the palm of hand and the cathode to the lower third of the forearm. In case of emotional disorders characterized by prevalence of anxiety, obsession, fear, inclination to suicide the treatment is made on the left side, and in case of prevalence of anguish, inhibition, flabbiness and apathy the treatment is made on the right side. The treatment lasts for 2 to 10 minutes with intervals of 3 to 7 days and, after the treatment course is completed, the treatment is repeated once every 3 to 4 months once or twice to prevent the relapse of depressions.

However, there are counterindications to the use of such a method, e.g. various cardiovascular diseases, foci of chronic infections; the prior art method is relatively counterindicative in case of diseases of rightside pair and non-pair organs and systems and hypertensive disease. The sensitivity threshold mainly depends on the electrical conductance properties of the skin and it may undergo substantial changes during the period of treatment action and can vary strongly in certain cases when determined in one and the same individual depending on the emotional condition and a number of subjective factors (e.g. a fear of an eventually painful treatment connected with earlier electric injuries or direct contact with electric current or, on the contrary, a certain bravado of an individual who tries to prove that he is really "the man"). This prior art method is used for a limited range of psychiatric patients under observation of medical personnel because of a danger of overdosage of the treatment action and related eventual side effects and complications. For this reason, this method is not used for the treatment of patients with neuroses, in the sexopathology, for the treatment and correction of superficial affective disorders in patients with borderline neuro-psychic disorders and also in practically healthy people involved in an emotionally intensive activity and persons with psychosomatic disorders. The prior art method does not allow treatment to be carried out with the simultaneous action upon the right and left hemispheres of the brain individually with different stimuli, and it does not make it possible to act upon the retina of the human eye with an optical radiation.

Known in the art is an apparatus comprising a pulse generator and electrodes (anode and cathode) connected to the pulse generator for carrying out the method (Electronic Pulse Stimulator. Description. 1973. Reklama Publishers. Kiev. pp. 3-5).

Also known in the art is a method for treating depressions (SU, A, 1274693), comprising, in order to accelerate the achievement of the therapeutical result, positioning electrodes unilaterally: the anode being positioned on the occipital-mastoidal region (behind the ear) and the cathode being positioned on the frontal region, determining the sensory threshold by increasing current intensity judging by the first sensation of current on the information from the individual, and stimulating the right or the left hemisphere of the brain with electric current with a pulse repetition rate ranging from 1 to 100 Hz during 7 to 15 minutes once every 2-3 days (8-10 times altogether), the treatment action being applied on the right side with emotional disorders characterized by prevalence of anxiety and the treatment action being applied on the left side with prevalence of anguish and apathy.

However, various cardiovascular diseases and foci of chronic infections are counterindications to this method. This prior art method does not allow the action to be applied simultaneously with different stimuli individually to the right and left hemispheres of the brain, nor does it allow the retina of the human eyes to be acted upon with an optical radiation.

Known in the art is an apparatus for carrying out the prior art method having electrodes (anode and cathode) (Electronic Pulse Stimulator. Description. 1973. Reklama Publishers, Kiev. pp. 3-5).

The prior art apparatus does not allow a treatment action to be applied simultaneously with different stimuli individually to the right and left hemispheres of the brain, nor does it allow the retina of the human eyes to be acted upon by an optical radiation.

Known in the art is a method for treating sexual disorders (SU,A, 1362483), comprising, in order to increase the number of frictions, positioning electrodes on the anterior and posterior surfaces of the metatarsal-tarsal articulation of the left foot, determining at the beginning of the stimulation the sensory excitability of the skin, and acting with electric current with a frequency ranging from 110 to 120 Hz and with a voltage 4-6 times as low as the sensitivity threshold during 2 to 3 minutes maximum 7 times.

However, as the treatment action is only addressed to the region of the right paracentral lobe, it would generally affect the functions of the urogenital system and has an antianxiety effect, provided the procedure is correct, but it cannot be used for the treatment of affective disorders in psychic patients and for treating the emotional conditions in practically healthy persons involving as the core condition such conditions as, e.g. anguish, apathy, inhibition, fear, perplexity, hypochondria, derealization, depersonalization or pathological symptoms (syndromes) connected with an increase in the level of functioning of morphofunctional systems of subdominant hemisphere of the brain with respect to symmetrical systems of the dominant hemisphere of the brain.

This prior art method does not make it possible to apply the treatment action individually to the right and left hemispheres of the brain simultaneously with different stimuli and does not allow the retina of the human eyes to be acted upon by an optical radiation.

Known in the art is an apparatus for carrying out the prior art method, comprising a pulse generator and electrodes. However, the prior art apparatus does not allow the treatment action to be applied individually to the right and left hemispheres of the brain simultaneously with different stimuli, nor does it allow the retina of the human eyes to be acted upon by an optical radiation.

The prior art methods and apparatuses (SU, A, 1303168; 1389774; 852336) make use of selective subsensory electrical stimulations of zones of the brain which contribute to the destruction of pathologically stable interhemispherical relations and to the formation of an alternative dominant activity determining to a large extent the condition of an individual and lasting for a long time.

With the use of the methods and apparatuses for lateral physiotherapy, there are counterindications to their use in patients with foci of chronic infections, hypertensive disease, and such treatment may give rise to side effects and complications because of inaccurate determination of intensity, dose and side of application and also because of unskilled definition of the psychic status of an individual. The prior art methods and apparatuses for lateral physiotherapy do not allow the right and left hemispheres of the brain to be acted upon individually simultaneously with different stimuli, nor do they allow the retina of the human eyes to be acted upon with a light flux.

Known in the art is a method for treating the emotional condition of an individual in treating seasonal affective disorders (Brit. J. Psychiatry. Vol. 147.No.10,1985. USA.Bethesda, Md., S. P. James, T. A. Wehr, P. A. Sack, B. T. Parry, N. E. Rosenthal. Treatment of Seasonal Affective Disorder with Light in the Evening. pp.424-428), comprising acting with an optical radiation upon the retina of the eyes of an individual. The optical radiation is produced by a lamp positioned at a distance of 90 to 95 cm from the individual providing a light flux of 500 lx. The treatment action is applied daily during one week within the period from 18.00 to 23.00 or from 7.00 to 12.00 hours depending on the habitual sleep pattern of the individual until the affective disorders are cut off.

The prior art method is not, however, effective in treating prolonged and weak psychogenic depressions and hypomanias, and it does not allow the right and left hemispheres of the brain to be acted upon individually simultaneously with different stimuli.

Known in the art is an apparatus for treating the emotional condition of an individual (Handbook of Photography. 1986. Tekhnika Publishers, Kiev; A. S. Gurlev. Arc Mercury Luminescent Lamps. p.72) comprising a mercury lamp placed in a glass bulb internally coated with a phosphor. The lamp is connected to an a.c. power supply at 115 V, with the current intensity of 0.8A. The lamp produces the light flux of 3400 lm.

The prior art apparatus does not allow the right and left hemispheres of the brain to be acted upon individually simultaneously with different stimuli.

SUMMARY OF THE INVENTION

It is an object of the invention to cut down the time for the treatment of a cyclotomic depression (seasonal affective disorder).

Another object of the invention is to reduce the side effects and complications caused by psychopharmacotherapy and lateral physiotherapy.

Further object of the invention is to enlarge the field of application of the method for treating the emotional condition of an individual, namely, to allow its use for the treatment of affective disorders in patients with alcoholism, schizophrenia, borderline neuropsychic psychosomatic disorders and in the sexopathology in practically healthy persons involved in an emotionally intensive activity such as operators, sportsmen, pedagogues.

One of the objects of the invention is to provide an apparatus for treating the emotional condition of an individual for carrying out the method according to the invention.

These objects are accomplished by that in a method for treating the emotional condition of an individual, comprising acting with an optical radiation upon the retina of the eyes of the individual, according to the invention, the optical radiation for each eye is formed in the form of two light fluxes: a light flux at wavelengths selected from a first wavelength range from $5.85 \times 10^{-7}$ to $7.60 \times 10^{-7}$ m and a light flux at wavelengths selected from a second wavelength range from $3.80 \times 10^{-7}$ to $5.50 \times 10^{-7}$ m, with the boundary between these light fluxes extending in a plane which is about coincident with the sagittal plane of the eye, and also by that with emotional conditions having as the core condition at least one of the following conditions: anguish (melancholia), apathy, flabbiness, inhibition, fear, horror, perplexity, hypochondria, derealization, depersonalization the lefthand halves of the retinas of both eyes are acted upon with a light flux at wavelengths selected from the first wavelength range and the righthand halves of the retinas of both eyes are simultaneously acted upon with a light flux at the wavelengths selected from the second wavelength range, and by that with emotional conditions including as the core condition one of the following conditions: anxiety, strain, hypomania, malice, suspicion, obsession, irascibility the lefthand halves of the retinas of both eyes are acted upon with a light flux at wavelengths selected from the second wavelength range and the righthand halves of the retinas of both eyes are acted upon simultaneously with a light flux at wavelengths selected from the first wavelength range, the treatment action being applied at least during a period until the disappearance of the subjective sensation of a distinct boundary separating the light fluxes, the treatment action being repeated at least once.

It is preferred that the light fluxes for both eyes be formed using light filters.

It is preferred that two auxiliary light fluxes be formed for each eye: an auxiliary light flux at wavelengths selected from a third wavelength range from $5.10 \times 10^{-7}$ to $5.60 \times 10^{-7}$ m and an auxiliary light flux at wavelengths selected from a fourth wavelength range from $5.70 \times 10^{-7}$ to $6.00 \times 10^{-7}$ m, with the boundary separating these light fluxes extending in a plane which is about coincident with the sagittal plane of the eye, the righthand or lefthand halves of the retinas of the eyes being simultaneously acted upon with the auxiliary light flux at wavelengths selected from the third wavelength range before these halves of the retinas of the eyes are acted upon with the light flux at wavelengths selected from the first wavelength range, and the righthand and lefthand halves of the retinas of the eyes being acted upon with the auxiliary light flux with wavelengths selected from the fourth wavelength range before these halves of the retinas of the eyes are acted upon with a light flux at wavelengths selected from the second wavelength range, the treatment actions being applied for at least a period until the disappearance of the subjective sensation of a distinct boundary separating the light fluxes, the treatment action being repeated at least once.

These objects are also accomplished by that in a method for treating the emotional condition, comprising acting with an optical radiation upon the retinas of both eyes of an individual, according to the invention, the optical radiation is formed for each eye in the form of two light fluxes: a light flux at wavelengths selected from a fifth wavelength range from $5.50 \times 10^{-7}$ to $6.20 \times 10^{-7}$ m and a light flux at wavelengths selected from a sixth wavelength range from $4.80 \times 10^{-7}$ m to $5.40 \times 10^{-7}$ m, with the boundary separating these light fluxes extending in a plane drawn about in parallel with the sagittal plane of the eye, and with emotional conditions including as the core condition at least one of the following conditions: anguish (melancholia), apathy, flabbiness, inhibition, fear, horror, perplexity, hypochondria, derealization, depersonalization the lefthand halves of both eyes are acted upon with a light flux at a wavelength selected from a fifth wavelength range and the righthand halves are acted upon simultaneously with a light flux at wavelengths selected from a sixth wavelength range, and with emotional conditions having as the core conditions at least one of the following conditions: anxiety, strain, hypomania, malice, suspicion, obsession, irascibility, the lefthand halves of the retinas of both eyes are acted upon with a light flux at wavelengths selected from the sixth wavelength range and the righthand halves of the retinas of both eyes are simultaneously acted upon with a light flux at wavelengths selected from the fifth wavelength range, the treatment action being applied for at least a period until disappearance of the subjective sensation of a distinct boundary separating the light fluxes, the treatment action being repeated at least once.

The above objects are accomplished by that in an apparatus for treating the emotional condition of an individual, comprising a light source, according to the invention, there is provided at least one light filter having at least two areas separated by a boundary which can be positioned simultaneously in a plane about coincident with the sagittal plane of the eye and in a plane drawn about in parallel with the frontal plane, the first area letting through from the light source a light flux at wavelengths selected from a wavelength range from $5.85 \times 10^{-7}$ m to $7.60 \times 10^{-7}$ m and the second area letting through from the light source a light flux at wavelengths selected from a wavelength range from $3.80 \times 10^{-7}$ to $5.50 \times 10^{-7}$ m, at least one light filter being positionable between the light source and the eye in the closest possible proximity to the eye in such a manner that at least one point of each area of the light filter be in one plane which is about perpendicular with respect to the sagittal plane of the eye.

These objects are also accomplished by that in an apparatus for treating the emotional condition of an individual, comprising a light source, according to the invention, there is provided at least one light filter having at least two areas separated by a boundary which is positionable simultaneously in a plane about coincident with the sagittal plane of the eye and in a plane drawn about in parallel with the frontal plane, the first area letting through from the light source a light flux at wavelengths selected from a wavelength range from $5.70 \times 10^{-7}$ to $6.00 \times 10^{-7}$ m and the second area letting through from the light source a light flux at wavelengths selected from a wavelength range from $5.10 \times 10^{-7}$ to $5.60 \times 10^{-7}$ m, at least one light filter being positionable between the light source and the eye in the closest possible proximity to the eye in such a manner that at least one point of each area of the light filter be in one plane which is about perpendicular with respect to the sagittal plane of the eye.

The above objects are also accomplished by that in an apparatus for treating the emotional condition of an individual comprising a light source, according to the invention, there is provided at least one light filter having at least two areas separated by a boundary which can be positioned simultaneously in a plane about coincident with the sagittal plane of the eye and in a plane drawn about in parallel with the frontal plane, the first area letting through from the light source a light flux at wavelengths selected from a wavelength range from $5.50 \times 10^{-7}$ to $6.20 \times 10^{-7}$ m and the second area letting through from the light source a light flux at wavelengths selected from a wavelength range from $4.80 \times 10^{-7}$ to $5.40 \times 10^{-7}$ m, at least one light filter being positionable between the light source and the eye in the closest possible proximity to the eye in such a manner that at least one point of each area of the light filter be positioned in one plane which is about perpendicular with respect to the sagittal plane of the eye.

At least one light filter is preferably made in the form of a contact lens.

An apparatus for treating the emotional condition preferably comprises one light filter for each eye in the form of a contact lens, the areas of the light filter located on the left from the boundaries separating the areas letting through a light flux at wavelengths selected from one wavelength range and the areas of the light filter located on the right from the boundary letting through a light flux at wavelengths selected from another wavelength range.

At least one light filter may be provided with a spectacles mounting.

An apparatus for treating the emotional condition of an individual is preferably provided with a pair of light filters fixed in a spectacles mounting, the areas of the light filters located on the left from the boundary separating the areas letting through a light flux at wavelengths selected from one wavelength range, and the areas of the light filters located on the right from the boundary separating the areas letting through a light flux at wavelengths selected from the other wavelength range.

This construction of the apparatus according to the invention for carrying out the method for treating the emotional condition of an individual ensures the use of weak physiologically adequate stimuli, makes it possible to reduce side effects and complications caused by psychopharmacotherapy and lateral physiotherapy and implies an accurate dosage of treatment actions so that it can be used in the borderline psychiatry, psychosomatic medicine, and sports and allows treatment time of superficial and prolonged emotional disorders to be cut down.

The method and apparatus for treating the emotional condition of an individual allow side effects and complications caused by psychopharmacotherapy and lateral physiotherapy with subsensory electrostimulations to be reduced with their individual use or with their use in combination with psychopharmacotherapy in patients with cyclotomy, seasonal affective disorders, schizophrenia, alcoholism, borderline neuropsychic disorders and psychosomatic disorders.

The absence of complications and a fair tolerance to the action with light fluxes at different wavelengths simultaneously and individually upon the right-and lefthand halves of the retinas of the eye, the occurrence of a slight sedative or euphorizing effect during the treatment action explain the favourable emotionally tinged reaction of an individual and allow the method and apparatus for treating the emotional condition to be used for practically healthy people involved in emotionally intensive activity such as sportsmen, operators and pedagogues as a personal use device for optimizing the mood and psychic condition.

BRIEF DESCRIPTION OF THE DRAWINGS

These and other objects of the invention will become apparent from the following specific embodiments illustrated in the accompanying drawings, in which.

DETAILED DESCRIPTION OF THE INVENTION

Figure 4:
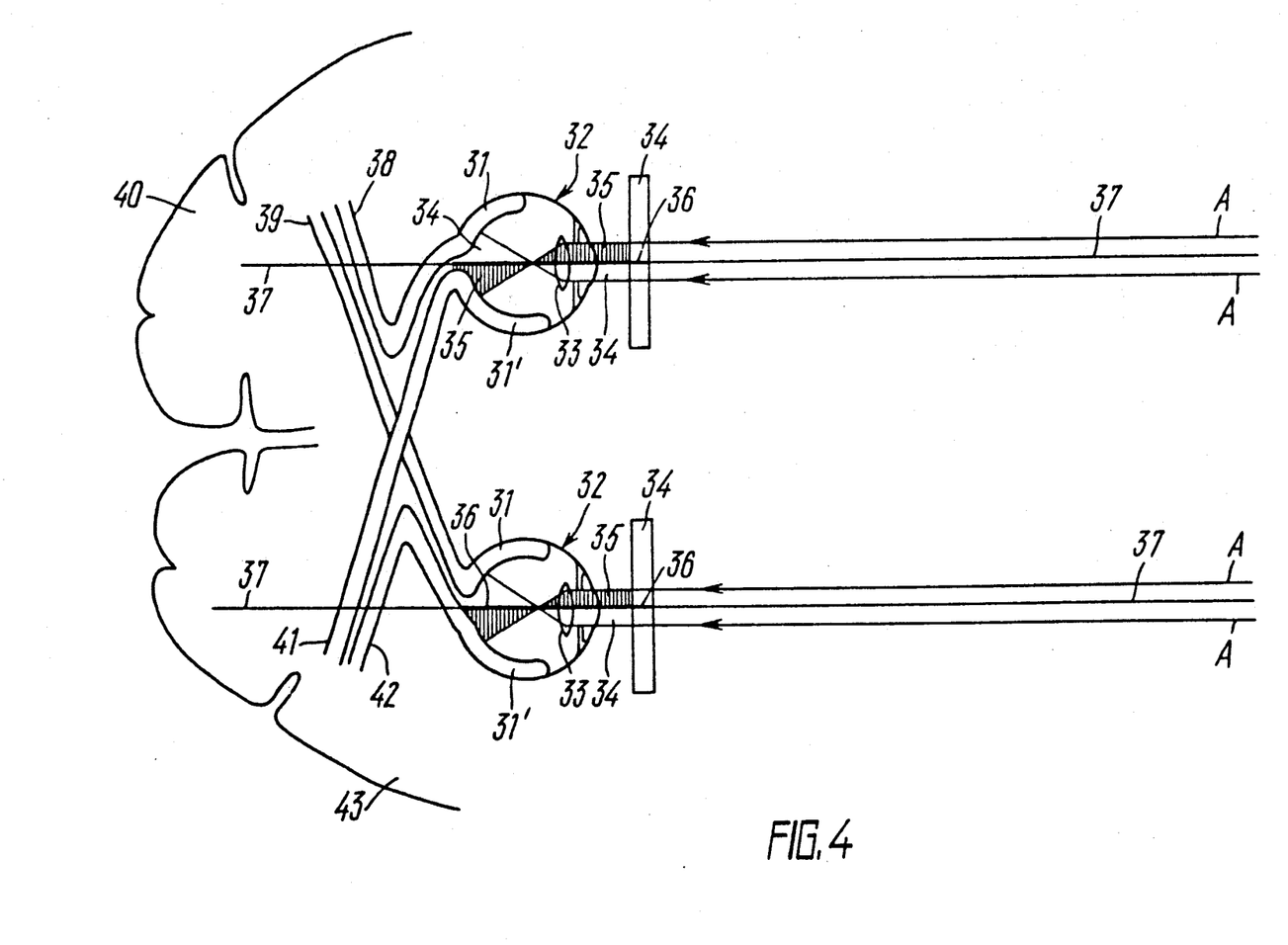
FIG. 4 shows light fluxes at different wavelengths acting upon the right- and lefthand halves of the retinas of the eye and schematic paths of different stimuli from the eye retinas to the left and right hemispheres of the brain with conditions of an individual defining a first group of conditions according to the invention.
Figure 5:
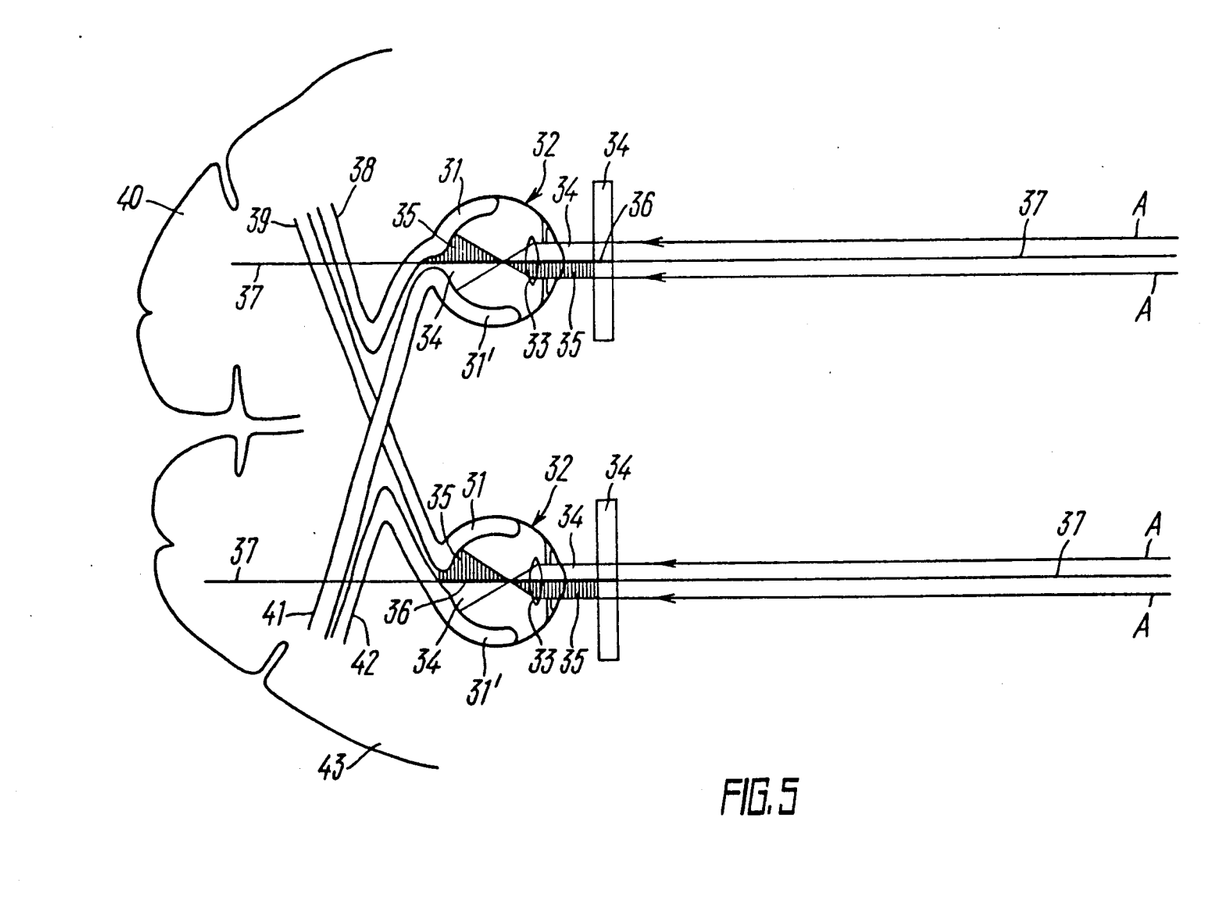
FIG. 5 shows light fluxes at different wavelengths acting upon the right- and lefthand halves of the retinas of the eye and schematic paths of different stimuli from the retinas of the eyes to the left and right hemispheres of the brain with conditions of an individual defining a second group of conditions.

Reference is first made to FIGS. 4 and 5 for explaining the gist of the invention.

A method for treating the emotional condition of an individual according to the invention resides in the following. Lefthand halves 31 and righthand halves 31' (FIG. 4) of the retinas of the eyes 32 of an individual having the crystalline lens 33 are acted upon with an optical radiation A. The optical radiation incident upon each eye 32 is formed as light fluxes 34, 35.

A boundary 36 separating the light fluxes 34, 35 extends between the light fluxes. The boundary 36 separating the light fluxes 34, 35 extends in a plane which is about coincident with a sagittal plane 37 of the eye 32.

With emotional conditions (a first group) having as the core condition at least one of the following conditions: anguish (melancholia), apathy, flabbiness, inhibition, fear, horror, perplexity, hypochondria, derealization, depersonalization the lefthand halves 31 of the retinas of both eyes 32 are acted upon with the light flux 34 and the righthand halves 31' of the retinas of both eyes 32 are simultaneously acted upon with the light flux 35.

The light flux 34 is at wavelengths selected from a wavelength range from $5.85 \times 10^{-7}$ to $7.60 \times 10^{-7}$ m. The light flux 35 is at wavelengths selected from a wavelength range from $3.80 \times 10^{-7}$ to $5.10 \times 10^{-7}$ m.

With emotional conditions (a second group) having as the core condition one of the following conditions: anxiety, strain, hypomania, malice, suspicion, obsession, irascibility the righthand halves 31' of the retinas of both eyes 32 (FIG. 4) are acted upon with the light flux 34 and the lefthand halves 31 of the retinas of both eyes 32 are simultaneously acted upon with the light flux 35.

The light flux 34, depending on the type of treatment action, may be at wavelengths selected from wavelength from $5.85\times10^{-7}$ to $7.60\times10^{-7}$ for carrying out the method claimed in claim 1, from $5.10\times10^{-7}$ to $5.60\times10^{-7}$ m for carrying out the method according to claim 3, and from $5.50\times10^{-7}$ to $6.20\times10^{-7}$ m for carrying out the method according to claim 4.

The light flux 35, depending on the group of conditions of an individual, may be at wavelengths selected from wavelength ranges, e.g. from $3.80\times10^{-7}$ to $5.50\times10^{-7}$ m for carrying out the method according to claim 1, from $5.70\times10^{-7}$ to $6.00\times10^{-7}$ m for carrying out the method according to claim 3, and from $4.80\times10^{-7}$ to $5.40\times10^{-7}$ m for carrying out the method according to claim 4.

We have found by way of experiments that conditions having as the core condition at least one of the following conditions: anguish (melancholia), apathy, flabbiness, inhibition, fear, horror, perplexity, hypochondria, derealization, depersonalization can be most advantageously treated by simultaneously acting upon the lefthand halves 31 of the retinas (FIG. 4) of the eyes 32 with the light flux 34 at wavelengths selected from the wavelength range from $5.85\times10^{-7}$ to $7.60\times10^{-7}$ m and upon the righthand halves 31' of the retinas of the eyes 32 with the light flux 35 at wavelengths selected from the wavelength range from $3.80\times10^{-7}$ to $5.10\times10^{-7}$ m. Conditions having as the core condition at least one of the following conditions: anxiety, strain, hypomania, malice, suspicion, obsession, irascibility can be most advantageously treated by simultaneously acting upon the lefthand halves 31 (FIG. 5) of the retinas of the eyes 32 with the light flux 35 at wavelengths selected from the wavelength range from $3.80\times10^{-7}$ to $5.50\times10^{-7}$ m and upon the righthand halves 31' of the retinas of the eyes 32 with the light flux 34 at wavelengths selected from the wavelength range from $5.85\times10^{-7}$ to $7.60\times10^{-7}$ m.

The treatment action is applied for at least a period until disappearance of the subjective sensation of a distinct boundary between the light fluxes (sensation of difference in colours): from 30 seconds to 50 minutes on the average as the treatment action applied for a time shorter than 30 seconds cannot have any appreciable effect on the emotional condition of an individual, and the treatment action applied for a time longer than 50 minutes may give rise to side effects in the form of blurred flabbiness, sleepiness, vertigo. As no complications occurred in using the method and apparatus for treating the emotional condition of an individual, they can be used for a long time with the treatment action being repeated at least once. The need to apply repeated treatment actions depends on a specific emotional condition of an individual, the individual's will and expediency of carrying out the treatment of the emotional condition of a given individual.

We have found by way of experiments that the result of a single treatment action by the method according to the invention starts manifesting itself during the period of three to twelve hours. If necessary, the treatment actions can be repeated maximum four times per 24 hours.

With the emotional conditions of the first group, the light flux 34 is transformed in the lefthand halves 31 (FIG. 4) of the retinas of both eyes 32 into electric signals propagating through conducting vision paths 38, 39 to the left hemisphere 40 of the brain; at the same time, the light flux 35 is transformed in the righthand halves 31' of the retinas of the eyes 32 into electric signals propagating through conducting vision paths 41, 42 to the right hemisphere 43 of the brain. This results in the emotional conditions of the first group in an individual being reduced or disappearing after at least one treatment action in three to twelve hours.

With the emotional conditions of the second group, the light flux 34 is transformed in the righthand halves 31' (FIG. 5) of the retinas of both eyes 32 into electric signals propagating through conducting vision paths 41, 42 to the right hemisphere 43 of the brain, and the light flux 35 is simultaneously transformed in the lefthand halves 31 of the retinas of the eyes 32 into electric signals propagating through conducting vision paths 39 to the left hemisphere 40 of the brain. This results in the emotional conditions of the second group in an individual being reduced or disappearing after at least one treatment action in three to twelve hours. The light fluxes 34, 35 are formed for both eyes 32 using light filters 44, 45 (FIGS. 4,5).

A preliminary action with auxiliary light fluxes 34, 35 proved to enhance the result obtained after the subsequent action with the light fluxes 34, 35 at wavelengths selected from wavelength ranges from $5.85\times10^{-7}$ to $7.60\times10^{-7}$ m and from $3.80\times10^{-7}$ to $5.10\times10^{-7}$ m, respectively. The method for treating the emotional condition of an individual is distinguished in this case in that, before acting upon the lefthand halves 31 of the retinas of the eyes 32 with the light flux 34 (FIG. 4) and upon the righthand halves 31' of the retinas of the eyes 32 with the light flux 34, the lefthand halves 31 of the retinas of the eyes 32 are acted upon with the auxiliary light flux 34 at wavelengths selected from the wavelength range from $5.10\times10^{-7}$ to $5.60\times10^{-7}$ m simultaneously with the action upon the righthand halves 31' of the retinas of the eyes 32 with the auxiliary light flux 35 at wavelengths selected from the wavelength range from $5.70\times10^{-7}$ to $6.00\times10^{-7}$ m. Accordingly, before acting upon the righthand halves 31' of the retinas of the eyes 32 with the light flux 34 (FIG. 5) and upon the lefthand halves 31 of the retinas of the eyes 32 with the light flux 35, the righthand halves 31' of the retinas of the eyes 32 are acted upon with the auxiliary light flux 34 at wavelengths selected from the wavelength range from $5.10\times10^{-7}$ to $5.60\times10^{-7}$ m and the lefthand halves 31 of the retinas of the eyes 32 are simultaneously acted upon with the auxiliary light flux 35 at wavelengths selected from the wavelength range from $5.7\times10^{-7}$ to $6.00\times10^{-7}$ m.

The treatment action is carried out for at least a period until the disappearance of the subjective sensation of a distinct boundary separating the light fluxes (sensation of a difference in colours) during from 30 seconds to 15 minutes on the average.

The treatment action applied for a time shorter than 30 seconds with the auxiliary light fluxes cannot enhance the result of the subsequent treatment action with other light fluxes 34, 35, and the treatment action with the auxiliary light fluxes 34, 35 for a time longer than 15 minutes may result in an impairment of the result from the application of the treatment action using other light fluxes.

In cases where an individual determines the action with a light flux at wavelengths selected from the wavelength range from $5.85\times10^{-7}$ to $7.60\times10^{-7}$ m and from $3.80\times10^{-7}$ to $5.10\times10^{-7}$ m as subjectively imperceptible, the treatment action can be applied using light fluxes at wavelengths selected from the wavelength ranges from $4.80\times10^{-7}$ to $5.10\times10^{-7}$ m and from $5.50\times10^{-7}$ to $6.20\times10^{-7}$ m.

With emotional conditions having as the core condition at least one of the following conditions: anguish (melancholia), apathy, flabbiness, inhibition, fear, horror, perplexity, derealization, depersonalization, the lefthand halves 31 of the retinas of both eyes 32 are acted upon with the light flux 34 and the righthand halves 31' of the retinas of the eyes 32 are acted upon simultaneously with the light flux 35. The light flux 34 is at wavelengths selected from the wavelength range from $5.50 \times 10^{-7}$ to $6.20 \times 10^{-7}$ m. The light flux 35 is at wavelengths selected from the wavelength range from $4.80 \times 10^{-7}$ to $5.10 \times 10^{-7}$ m.

With emotional conditions having as the core conditions at least one of the following conditions: anxiety, strain, hypomania, malice, suspicion, obsession, irascibility, the lefth and halves 31 of the retinas of both eyes 32 are acted upon with the light flux 35 and the righthand halves 31' of the retinas of both eyes 32 are simultaneously acted upon with the light flux 34.

The treatment action is carried out during a period until the disappearance of the subjectively perceived difference in colours, during from 2 minutes to two hours on the average.

It has been found by way of experiments that the treatment action applied for a time shorter than 2 minutes cannot bring about any appreciable result, and an increase in the duration of the treatment action in excess of two hours cannot bring about a confident enhancement of the result achieved by that time.

Therefore, the implementation of the method according to the invention makes it possible to apply treatment actions individually to the right and left hemispheres of the brain with different stimuli, whereby the time for curing cyclotomic depression (seasonal affective disorder) can be cut down, side effects and complications caused by psychopharmacotherapy and lateral physiotherapy can be reduced, and the field of application of the method and apparatus for treating the emotional condition of an individual according to the invention may be extended to the treatment of affective disorders in patients with alcoholism, schizophrenia, borderline neuropsychic and psychosomatic disorders, in the sexopathology and in practically healthy persons involved in emotionally intensive activities such as operators, sportsmen, pedagogues.

Various embodiments of an apparatus for carrying out the method according to the invention will now be described in detail.

An apparatus for treating the emotional condition of an individual according to the invention comprises a light source 1 (FIG. 1), and a pair of light filters 2. Each light filter 2 has at least two areas 3,4 separated by a boundary 5 which can be positioned at one and the same time in a plane which is about coincident with a sagittal plane 6 of an eye 7 and in a plane 8 drawn about in parallel with a frontal plane 9.

The area 4 of each light filter 2 lets through from the light source 1 a light flux 10 at wavelengths selected from a first wavelength range from $5.85 \times 10^{-7}$ to $7.60 \times 10^{-7}$ m, and the area 3 lets through from the light source 1 a light flux 11 at wavelengths selected from a second wavelength range from $3.80 \times 10^{-7}$ to $5.50 \times 10^{-7}$ m, at least one light filter 2 being adapted to be positioned between the light source 1 and the eye 7 at a distance of its maximum proximity to the eye in such a manner that at least one point 12 of the area 4 of the light filter 2 and a point 13 of the area 3 of the light filter 2 are in one plane 14 drawn about perpendicularly with respect to the sagittal plane 6 of the eye 7. The planes 14 and 8 coincide with each other in FIG. 1.

Figure 1:
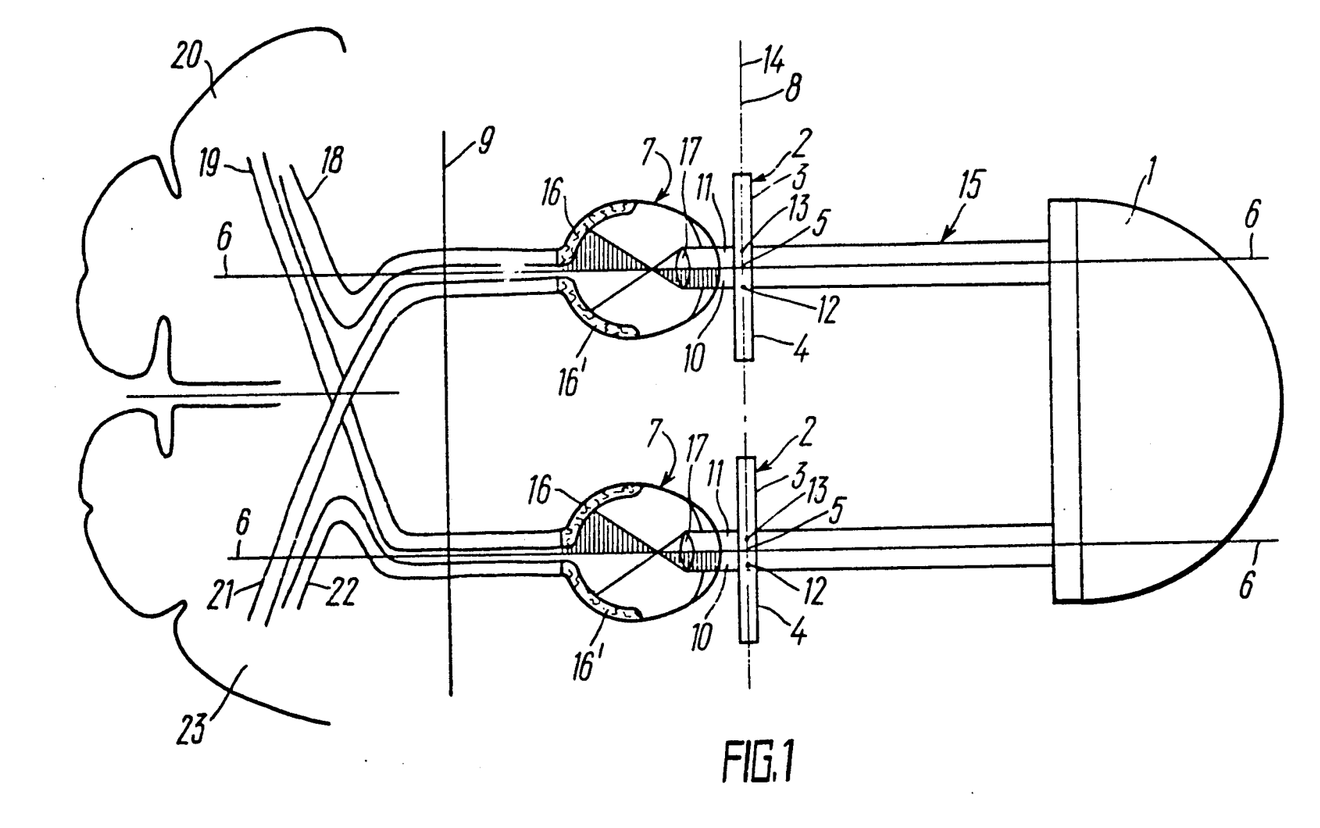
FIG. 1 schematically shows an apparatus for treating the emotional condition of an individual according the invention.

An optical radiation, 15 from the light source 1 acts upon lefthand halves 16 and righthand halves 16' of the retinas of the eye having a crystalline lens 17.

The lefthand halves 16 of the retinas of both eyes 7 connect through conducting vision paths 18, 19 to the left hemisphere 20 of the brain.

The righthand halves 16' of the retinas of both eyes 7 connect through conducting vision paths 21, 22 to the right hemisphere 23 of the brain.

Figure 2:
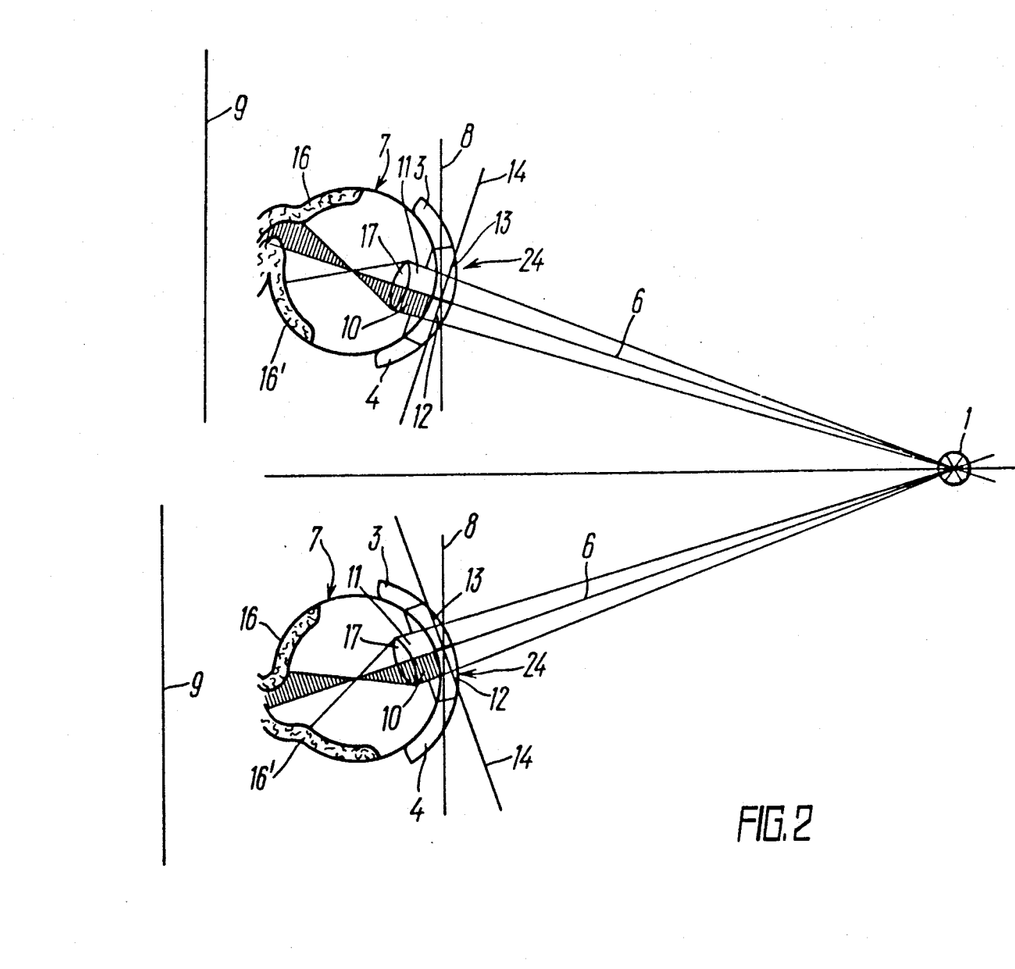
FIG. 2 schematically shows an apparatus for treating the emotional condition of an individual having light filters in the form of contact lenses according to the invention.

At least one light filter 2 may be made in the form of a contact lens 24 (FIG. 2).

Figure 3:
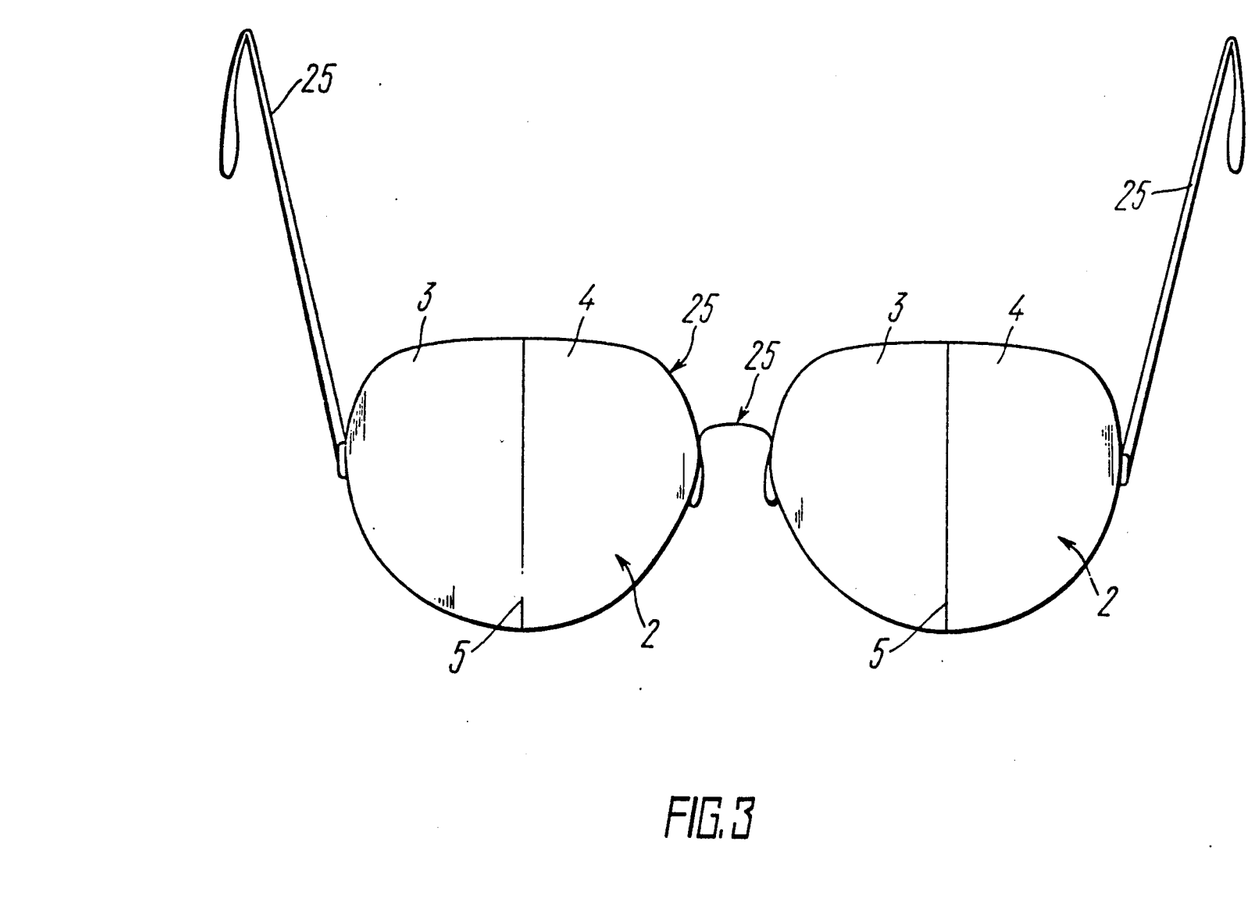
FIG. 3 schematically shows light filters of an apparatus for treating the emotional condition of an individual according to the invention fixed in a spectacles mounting.

At least one light filter 2 may also be provided with a spectacles mounting 25 (FIG. 3).

Operation of the apparatus for treating the emotional condition of an individual according to the invention is as follows.

The emotional condition of an individual is first determined using one of appropriate known techniques, e.g. clinically by applying a standard evaluation of psychic disorders, by means of experimental psychological procedures as well as by interviewing a practically healthy individual, observing behaviour of the individual and carrying out analysis of information obtained from the individual as a result of self-observation.

After the determination of the emotional condition of the individual, the light source 1 (FIG. 1) is placed before the latter's eyes to produce the optical radiation 15. At least one light filter 2 is placed at a distance of the closest possible proximity to the eye 7. The boundary 5 separating the areas 3 and 4 of the light filter 2 is positioned to extend in a plane about coincident with the sagittal plane 6 of the eye 7 and simultaneously in the plane 8 which runs about in parallel with the frontal plane 9.

At least one point 12 of the area 4 of the light filter 2 and at least one point 13 of the area 3 of the light filter 2 are positioned in one and the same plane 14 which is drawn about perpendicularly with respect to the sagittal plane 6 of the eye 7. The optical radiation 15 is formed by means of the light filter 2 as light fluxes 10 and 11. The light flux 10 acts upon the lefthand halves 16 of the retinas of the eyes 7 and the light flux 11 simultaneously acts upon the righthand halves 16' of the retinas of both eyes 7, the treatment action being repeated at least once.

Depending on emotional condition of an individual, various combinations of the areas 3,4 of the light filters 2 are possible to let through wavelengths selected from the following wavelength ranges: $5.85 \times 10^{-7}$ to $7.60 \times 10^{-7}$ m; from $3.80 \times 10^{-7}$ to $5.50 \times 10^{-7}$ m; from $5.10 \times 10^{-7}$ to $5.60 \times 10^{-7}$ m; from $5.70 \times 10^{-7}$ to $6.00 \times 10^{-7}$ m; from $5.50 \times 10^{-7}$ to $6.20 \times 10^{-7}$ m; from $4.80 \times 10^{-7}$ to $5.40 \times 10^{-7}$ m.

With emotional conditions including as the core condition at least one of the following conditions: anguish (melancholia), apathy, flabbiness, inhibition, fear, horror, perplexity, hypochondria, derealization, depersonalization (a first group of conditions) the light filters 2 are placed before an individual eyes (the first combination) in which the areas 4 let through the light fluxes 10 at wavelengths selected from the first wavelength range from $5.85 \times 10^{-7}$ to $7.60 \times 10^{-7}$ m and the areas 3 let through the light flux 11 at wavelengths selected from the second wavelength range from $3.80 \times 10^{-7}$ to $5.50 \times 10^{-7}$ m. The action is applied during at least a period until the subjective sensation of a distinct boundary between the light fluxes (difference in colours) disappears during from 30 seconds to 50 minutes on the average. The optical radiation 15 from the light source 1 is then interrupted, and the light source 1 and the light filters 2 are removed.

In cases an individual determines the action with the light fluxes 10, 11 let through by the light filters 2 (the first combination) as subjectively imperceptible, with the emotional conditions of the first group the light filters 2 (the second combination) are placed before the eyes of the individual in which the areas 4 let through the light fluxes 10 at wavelengths selected from the wavelength range from $5.50 \times 10^{-7}$ to $6.20 \times 10^{-7}$ m and the areas 3 which let through the light flux 11 at wavelengths selected from the wavelength range from $4.80 \times 10^{-7}$ to $5.40 \times 10^{-7}$ m. The treatment action is applied for at least a period until the subjective sensation of a difference in colours disappears, during from 2 minutes to two hours on the average, and the optical radiation 15 from the light source 1 is then interrupted and the light source 1 and light filters 2 are then removed.

To enhance the effect of the treatment action with the light fluxes 10, 11 let through by the light filters 2 (the first combination), the light filters 2 (the third combination) are preliminarily placed before the eyes of an individual, in which the areas 4 let through the auxiliary light fluxes 10 at wavelengths selected, e.g. from the third wavelength range from $5.10 \times 10^{-7}$ to $5.60 \times 10^{-7}$ m and the areas 3 simultaneously let through the auxiliary light fluxes 11 at wavelengths, e.g. selected from the fourth wavelength range from $5.70 \times 10^{-7}$ to $6.00 \times 10^{-7}$ m. The action is applied for at least a period until the subjective sensation of a distinct boundary between the light fluxes disappears (sensation of difference in colours), during from 30 seconds to 15 minutes on the average. The treatment action is then applied with the light fluxes 10, 11 let through the light filters 2 (the first combination).

With emotional conditions having as the core condition at least one of the following conditions: anxiety, strain, malice, suspicion, hypomania, obsession, irascibility (the second group of conditions), the light filters 2 (the fourth combination) are placed before the eyes of an individual, in which the areas 4 let through the light fluxes 10 at wavelengths selected from the wavelength range from $3.80 \times 10^{-7}$ to $5.50 \times 10^{-7}$ m and the areas 3 let through the light fluxes 11 at wavelengths selected from the wavelength range from $5.85 \times 10^{-7}$ to $7.60 \times 10^{-7}$ m. The treatment action is applied for at least a period until the disappearance of the subjective sensation of a difference in colours, during from 30 seconds to 50 minutes on the average. The optical radiation 14 from the light source 1 is then interrupted and the light source 1 and the light filters 2 are removed. In cases an individual determines the action with the light fluxes let through by the light filters 2 (the fourth combination) as subjectively imperceptible, with the emotional conditions of the second group the light filters 2 (the fifth combination) are placed before the eyes of the individual in which the areas 4 let through the light fluxes 10 at wavelengths selected from the wavelength range from $4.80 \times 10^{-7}$ to $5.40 \times 10^{-7}$ m, and the areas 3 let through the light fluxes 11 at wavelengths selected from the wavelength range from $5.50 \times 10^{-7}$ to $6.20 \times 10^{-7}$ m.

The action is applied during at least a period until the disappearance of the subjective sensation of a difference in colours, during from two minutes to two hours on the average. The optical radiation 15 from the light source 1 is then interrupted, and the light source 1 and the light filters 2 are removed.

To enhance the effect of the light fluxes 10, 11 let through by the light filters 2 (the fourth combination), the light filters 2 (the sixth combination) are preliminarily placed before the eyes of an individual, in which the areas 4 let through the auxiliary light fluxes 10 at wavelengths selected from the wavelength range from $5.70 \times 10^{-7}$ to $6.00 \times 10^{-7}$ and the areas 3 simultaneously let through the auxiliary light fluxes 11 at wavelengths selected from the wavelength range from $5.10 \times 10^{-7}$ to $5.60 \times 10^{-7}$ m.

The treatment action is applied for at least a period until the disappearance of the subjective sensation of a difference in colours, from 30 seconds to 15 minutes on the average. The treatment action is then applied by acting with the light fluxes 10,11 let through the light filters 2 (the fourth combination).

If the light filter 2 for each eye 7 is made in the form of a contact lens 24 (FIG. 2), the areas 4 of the light filter 2 located on the left from the boundaries 5 separating the areas 3,4 let through the light flux 11 at wavelengths selected from one wavelength range and the areas 3 of the light filters 2 located on the right from the boundary 5 separating the areas 3,4 let through the light flux 10 at wavelengths selected from another wavelength range.

If the apparatus has a pair of the light filters 2 fixed in a spectacles mounting 25 (FIG. 3), the areas 4 of the light filters 2 (FIG. 1) located on the left from the boundary 5 separating the areas 3,4 let through the light flux 11 at wavelengths selected from one wavelength range and the areas 3 of the light filters 2 located on the right from the boundary 5 separating the areas 3,4 let through the light flux 10 at wavelengths selected from another wavelength range.

With emotional conditions of the first and second groups the light fluxes 10 are transformed in the lefthand halves 16 of the retinas of both eyes 7 into electric signals (stimuli) propagating through the conducting vision paths 18,19 into the left hemisphere 20 of the brain and the light fluxes 11 are simultaneously transformed in the righthand halves 16' of the retinas of the eyes 7 into electric signals (stimuli) propagating through the conducting vision paths 21,22 into the right hemisphere 23 of the brain. Depending on which one of the six versions of the light filters 2 (in terms of combinations of the areas 3,4) is placed before the eyes 7 of an individual, at least one treatment action with the light fluxes 10,11 upon the lefthand 16 and righthand 16' halves of the retinas of both eyes 7 results in the disappearance of the emotional conditions of the first or second group in the individual in a three to twelve hours time on the average.

The need to carry out a repeated treatment depends on specific emotional condition of an individual, the individual's will and expediency of correction of the emotional condition of the individual.

If necessary, it is preferred that the treatment action be repeated with a regularity of maximum four times in 24 hours.

As no complications were observed from the application of the apparatus for treating the emotional condition of an individual, the treatment can be used during a prolonged period.

Therefore, the use of the apparatus according to the invention makes it possible to apply a treatment action individually to the right 23 and left 20 hemispheres of the brain simultaneously with different stimuli so as to cut down the time for treating cyclotomic depression (seasonal affective disorder), reduce side effects and complications from psychopharmacotherapy and lateral physiotherapy and enlarge the field of application of the apparatus according to the invention for the treatment and correction of affective disorders in patients with alcoholism, schizophrenia, borderline neuropsychic and psychosomatic disorders; in the sexopathology; in practically healthy people involved in emotionally intensive activities: operators, sportsmen, pedagogues.

Examples of clinical application of the apparatus according to the invention for treating the emotional condition of an individual will be given below.

EXAMPLE 1

Female patient B, 31. Reactive depression developed after the death of a daughter. Clinically: manifest anguish affect, feeling of depression, poor appetite, motor and ideomotor inhibition.

The patient fixed to the psychotraumatic situation, spoke out irrational self-incriminations and suicidal thoughts.

The light source 1 producing the light flux of 1500 lm was placed at a distance of 1.3 m from the patient. The patient was invited to look fixedly at a point far from the patient to lower amplitude of the eye motions.

The light filters 2 fixed in the spectacles mounting 25 (FIG. 3) were placed in such a manner that each boundary 5 (FIG. 1) separating the light fluxes 10,11 for each eye 7 extend simultaneously in two planes: a plane about coincident with the sagittal plane 6 of the eye 7 and a plane 8 about parallel with the frontal plane 9. The areas 4 of the light filters 2 that let through the auxiliary light fluxes 10 at wavelengths from $5.20 \times 10^{-7}$ to $5.40 \times 10^{-7}$ m were located on the right from the boundaries 5 separating the light fluxes 10,11 with respect to the patient, and the areas 3 of the light filters 2 that let through the light flux at wavelengths from $5.75 \times 10^{-7}$ to $5.85 \times 10^{-7}$ m were located on the left from the boundaries 5 separating the light fluxes 10,11 with respect to the patient. The light source 1 was turned on.

The treatment action with the auxiliary light fluxes 10 upon the lefthand halves 16 of the retinas of the eyes 7 and simultaneously with the light fluxes 11 upon the righthand halves 16' of the retinas of the ayes 7 was applied during 3 minutes. Two minutes after the treatment action started, the patient told that the boundary between "green" and "yellow" halffields of vision "have blurred", and a single "yellow-green" colour prevailed in the vision field.

After the treatment action was interrupted, the light filters 2 were chosen having the areas 3,4 letting through the light flux 10 at subjectively most pleasant wavelengths from $6.70 \times 10^{-7}$ to $7.20 \times 10^{-7}$ m and the light flux 11 at subjectively most pleasant wavelengths from $4.40 \times 10^{-7}$ to $4.70 \times 10^{-7}$ m according to the patient.

The light filters 2 were replaced by the light filters 2 having the areas 4 and 3 letting through the light fluxes 10, 11 at wavelengths selected from the wavelength ranges from $5.85 \times 10^{-7}$ to $7.60 \times 10^{-7}$ m and from $3.80 \times 10^{-7}$ to $5.50 \times 10^{-7}$ m. The light filters 2 fixed in the spectacles mounting 25 (FIG. 3) were placed as described above.

The light source 1 (FIG. 1) was turned on and the lefthand halves 16 of the retinas of the eye were acted upon with the light fluxes 10 and the righthand halves 16' of the retinas of the eye were acted upon simultaneously with the light fluxes 11. In one minute and twenty seconds the patient said that the boundary separating the "red" and "blue" half-fields of vision started to acquire a "crimson" shade, lost distinctiveness and gradually enlarged to the right and left to fill up the central area of the vision field. The action was applied for 12 minutes, and the light source 1 was then turned off and the spectacles mounting 25 (FIG. 3) with the light filters 2 (FIG. 1) was removed. During the treatment action, the patient noted a certain relaxation, the ideomotor and motor inhibition eased. In 30–40 minutes after termination of the treatment action these changes in condition of the patient gradually disappeared and the condition become clinically close to the emotional condition prior to the treatment action. Seven hours after the termination of the treatment action the patient started helping medical personnel in cleaning of the premises and feeding of patients on her own initiative. The ideomotor and motor inhibition disappeared, anguish and depression substantially eased, and the patient took part in conversations with other patients and responded to jokes.

Next day these changes in the condition of the patient disappeared. Clinically: anguish affect, feeling of depression, poor appetite, motor inhibition. The patient was fixed to the psychotraumatic situation, suicidal thoughts disappeared, the irrational ideas of self-incrimination were slightly disclosured. The action with the light fluxes 10,11 upon the retinas of the eyes 7 was applied on the patient's request. Fourteen such treatment actions were applied altogether. The modes and parameters are given in Table 1.

The psychopathological symptoms: anguish, feeling of depression disappeared after the 12th treatment action. The patient started criticizing her pathological ideas that she expressed earlier. Sleep and appetite normalized.

No side effects and complications reported as caused by psychopharmacotherapy occurred in the patient during the treatment of her emotional condition using the apparatus according to the invention.

The patient was discharged in good condition, and she continued to work at her permanent employment. The patient did not turn to the psychiatrist during two years of dynamic observation and there were no complaints or psychopathological symptoms. The patient was put off the psychiatric record.

EXAMPLE 2

Male patient V,32. Cyclotomy. Complaints of anguish, indifference to work and amusement, heavy fatigue, increase in body weight. Clinically: anergia, weakening of emotional contact, inclination to a pessimistic interpretation of events, lower tempo of thinking processes, vocal-motor inhibition. The disease was characterized by cycles of changes of autumn-winter depressions, spring-summer hypomanias or euthymias.

All treatment actions in this Example were applied similarly to Example 1 using the apparatus according to the invention. Eight such treatment actions were applied altogether. The modes and parameters of the treatment actions are given in Table 2.

TABLE 1

| Treatment action No. 1 | Day 2 | Light flux from light source 1 (lm) 3 | Distance from individual's eyes 7 to light source 1 (m) 4 | Duration of action (minutes) 5 | Selected wavelength ranges of light fluxes 10, 11 acting upon: | |
|---|---|---|---|---|---|---|
| | | | | | left hand halves 16 of the retinas of both eyes 7 ($\times 10^{-7}$ m) 6 | righthand halves 16' of the retinas of both eyes 7 ($\times 10^{-7}$ m) 7 |
| 1 | 1 | 1500 | 1.3 | 3 | 5.20–5.40 | 5.75–5.85 |
| 2 | 1 | 1800 | 1.0 | 12 | 6.70–7.20 | 4.40–4.70 |
| 3 | 2 | 1500 | 1.2 | 4 | 5.20–5.50 | 5.75–5.85 |
| 4 | 2 | 1800 | 0.95 | 15 | 6.0–7.40 | 4.00–4.50 |
| 5 | 3 | 1700 | 1.1 | 5 | 5.10–5.40 | 5.75–5.85 |
| 6 | 3 | 2000 | 1.0 | 20 | 5.90–6.40 | 4.60–4.80 |
| 7 | 5 | 1600 | 1.3 | 5 | 5.10–5.40 | 5.75–5.85 |
| 8 | 5 | 1800 | 1.2 | 20 | 6.00–6.60 | 4.50–4.80 |
| 9 | 6 | 1800 | 1.0 | 3 | 5.20–5.50 | 5.80–5.90 |
| 10 | 6 | 2100 | 0.9 | 12 | 6.60–7.40 | 4.80–5.00 |
| 11 | 8 | 1600 | 1.2 | 2 | 5.20–5.40 | 5.80–5.90 |
| 12 | 8 | 1900 | 1.0 | 8 | 6.20–7.00 | 5.00–5.30 |
| 13 | 11 | 1400 | 1.0 | 1.5 | 5.10–5.40 | 5.80–5.90 |
| 14 | 11 | 1000 | 1.0 | 6 | 5.80–6.10 | 4.90–5.10 |

TABLE 2

| Treatment action No. 1 | Day 2 | Light flux from light source 1 (lm) 3 | Distance from the eyes 7 of an individual to light source 1 (m) 4 | Duration of treatment action (minutes) 5 | Selected wavelength ranges of light fluxes 10, 11 acting upon: | |
|---|---|---|---|---|---|---|
| | | | | | left hand halves 16 of the retinas of both eyes 7 ($\times 10^{-7}$ m) 6 | righthand halves 16' of the retinas of both eyes 7 ($\times 10^{-7}$ m) 7 |
| 1 | 1 | 1400 | 1.2 | 5 | 5.00–5.30 | 5.75–5.85 |
| 2 | 1 | 2000 | 1.0 | 20 | 5.90–6.40 | 4.70–5.00 |
| 3 | 2 | 1600 | 1.2 | 7 | 5.10–5.40 | 5.40–5.60 |
| 4 | 2 | 2100 | 1.0 | 30 | 6.60–7.40 | 4.30–4.70 |
| 5 | 3 | 1700 | 1.2 | 6 | 5.00–5.30 | 5.75–5.15 |
| 6 | 3 | 2200 | 1.0 | 25 | 6.00–6.70 | 4.70–4.90 |
| 7 | 5 | 1600 | 1.2 | 4 | 5.00–5.20 | 5.80–5.90 |
| 8 | 5 | 2100 | 1.0 | 17 | 5.90–6.10 | 4.90–5.10 |

The treatment was interrupted after the eighth treatment action in view of complete reduction of the affective disorders. The next unease condition 40 days after the treatment was cut off on the patient's request during four days using about the same mode of treatment actions.

The patient was discharged in good condition.

No side effects or complications were observed in the patient during the treatment using the apparatus according to the invention as would generally be the case in using psychopharmacotherapy.

EXAMPLE 3

Male patient G, 40. Suffered of low-progradient schizophrenia with the prevalence of affective disorders.

Clinically: affective disorders manifested in the form of superficial depressions with the predominance of obsessive and phobic transitory disorders. By the moment of examination the patient was anxious, strained, suspicious; he could not manage to fix an eye at one point for even a short time; the eyes glistened, "ran from side to side". The light filters 14 (FIG. 1) in the form of contact lenses 24 (FIG. 2) having the areas 4 letting through the light fluxes 10 at wavelengths within the range from $6.70 \times 10^{-7}$ to $7.60 \times 10^{-7}$ m selected from the wavelength range from $5.85 \times 10^{-7}$ to $7.60 \times 10^{-7}$ m and the areas 3 letting through the light fluxes 11 at wavelengths ranging from $3.80 \times 10^{-7}$ to $4.30 \times 10^{-7}$ m selected from the wavelength range from $3.80 \times 10^{-7}$ m to $5.50 \times 10^{-7}$ m were placed on the eyes 7 of the patient on his own accord. The boundary 5 separating the areas 3,4 of each light filter 2 was positioned to extent in the sagittal planes 6 of both eyes 7. The areas 4 were located on the right from the boundaries 5 separating the areas 3,4 and the areas 3 were located on the left from the boundaries 5 separating the areas 3,4 with respect to the patient. The light source 1 was turned on to produce the optical radiation 15 with the light flux of 800 lm and was placed at a distance of 1–1.5 m from the patient eyes 7 in such a manner that the optical radiation 15 cannot cause unpleasant sensations in the patient. The patient was invited to look at the light source 1. The light flux 10 acted upon the lefthand halves 16 of the retinas of both eyes and the light flux 11 acted simultaneously upon the righthand halves 16' of the retinas of both eyes 7 for 30 seconds. Thirty seconds after the beginning of the treatment action the patient said that the boundary between the blue and red lost distinction and "blurred" so that a crimson-pink colour was in the vision field. After the treatment action was terminated, the light source 1 was removed and the light filters 14 (FIG. 1) in the form of contact lenses 24 (FIG. 2) were also removed from the patient's eyes. After the treatment action the patient said that his condition "improved" and anxiety and internal strain eased. Suspicion became weaker, and the patient calmed down and became more communicative. This condition lasted for about one hour, and the depressive anxiety and strain then began to prevail again. However, 3–4 hours after that the state of anxiety and strain gradually disappeared, the patient calmed down and "internally relaxed" as he put it. Next day the patient informed about renewed anxiety and strain and asked that the treatment action be repeated. Twelve treatment actions were applied altogether. The modes and parameters of the treatment actions are given in Table 3. The duration of the treatment actions was at least equal to a time period during which the subjective difference between colours disappeared. The anxiety-depressive disorders were discoloured after the 5th treatment action.

In view of the manifest lability of the emotional condition in this patient suffering of alcoholism, especially during the first days of the postwithdrawal period, the treatment actions were applied taking into account the core emotional condition. After the sixth treatment action anxiety and strain gradually disappeared from the emotional condition of the individual. The treatment of anxiety-depressive disorders in the emotional condition of the alcoholic patient was successfully completed after the ninth treatment action.

TABLE 3

| Treatment action No. | Day | Light flux from light source 1 (lm) | Distance from eyes of individual to light source 1 (m) | Duration of treatment action (minutes) | Selected wavelength ranges of the light fluxes 10, 11 acting upon: | |
|---|---|---|---|---|---|---|
| | | | | | lefthand halves 16 of the retinas of both eyes 7 ($\times 10^{-7}$ m) | righthand halves 16' of the retinas of both eyes 7 ($\times 10^{-7}$ m) |
| 1 | 2 | 3 | 4 | 5 | 6 | 7 |
| 1 | 1 | 800 | 1.5 | 0.5 | 4.50–4.80 | 6.30–6.70 |
| 2 | 2 | 900 | 1.3 | 1 | 4.30–4.60 | 6.50–7.20 |
| 3 | 2 | 700 | 1.5 | 2 | 3.80–4.30 | 6.70–7.60 |
| 4 | 3 | 1000 | 1.3 | 4 | 4.50–4.80 | 6.20–6.60 |
| 5 | 3 | 700 | 1.5 | 6 | 4.30–4.60 | 6.50–7.20 |
| 6 | 5 | 800 | 1.3 | 0.5 | 4.50–4.80 | 5.90–6.20 |
| 7 | 6 | 1300 | 1.0 | 1 | 4.30–4.60 | 6.30–6.70 |
| 8 | 6 | 1300 | 1.0 | 2 | 4.30–4.60 | 6.50–7.20 |
| 9 | 6 | 700 | 1.3 | 4 | 3.80–4.30 | 6.70–7.60 |
| 10 | 8 | 800 | 1.3 | 6 | 4.30–3.60 | 6.50–7.20 |
| 11 | 10 | 1000 | 1.0 | 4 | 5.00–5.30 | 5.75–5.85 |
| 12 | 12 | 1500 | 0.95 | 4 | 4.50–4.80 | 5.90–7.20 |

TABLE 4

| Treatment action No. | Day | Light flux from light source 1 (lm) | Distance from the eyes 7 of individual to light source 1 (m) | Duration of treatment action (minutes) | Selected wavelength ranges of the light fluxes 10, 11 acting upon: | |
|---|---|---|---|---|---|---|
| | | | | | lefthand halves 16 of the retinas of both eyes 7 ($\times 10^{-7}$ m) | righthand halves 16' of the retinas of both eyes 7 ($\times 10^{-7}$ m) |
| 1 | 2 | 3 | 4 | 5 | 6 | 7 |
| 1 | 1 | 1800 | 1.5 | 20 | 4.90–5.10 | 6.80–7.40 |
| 2 | 2 | 1000 | 0.9 | 35 | 4.80–5.00 | 6.00–6.30 |
| 3 | 2 | 1400 | 1.2 | 50 | 4.00–4.60 | 6.90–7.60 |
| 4 | 3 | 1800 | 0.9 | 35 | 6.20–6.60 | 5.10–5.30 |
| 5 | 3 | 1600 | 1.1 | 50 | 4.60–4.90 | 6.20–6.80 |
| 6 | 4 | 2000 | 0.9 | 35 | 5.80–6.20 | 5.20–5.50 |
| 7 | 4 | 1400 | 1.2 | 20 | 4.80–5.00 | 6.00–6.30 |
| 8 | 5 | 2000 | 0.9 | 20 | 5.90–6.20 | 5.10–5.30 |
| 9 | 7 | 2000 | 0.9 | 20 | 6.00–6.30 | 5.20–5.50 |

The patient was discharged after the twelvth treatment action in view of the disappearance of the above-mentioned symptoms. No side effects or complications occurring in using psychopharmacotherapy and lateral physiotherapy as reported in literature were observed in the patient using the apparatus according to the invention for treating the emotional condition.

EXAMPLE 4

Male patient D, 40. Diagnosis: chronic alcoholism at the II phase, pseudoheavy drinking form; second phase of alcohol withdrawal syndrome. Complaints of a strong attraction to spirits, headaches, pains in the heart area vomiting in the mornings, sleeplessness. Clinically: irritable, strained and anxious.

Treatment with the aid of the apparatus according to the invention was started against the background of the detoxication therapy. All actions in this Example were applied as described in Example 1. Nine treatment actions were applied. The modes and parameters of the treatment actions are given in Table 4.

As psychopharmacotherapy or lateral physiotherapy were not used in addition to the detoxication therapy and correction of the emotional condition of this patient using the apparatus according to the invention, no side effects or complications reported in connection with the use of psychopharmacotherapy and lateral physiotherapy occurred in the patient.

EXAMPLE 5

Male patient A, 48. Suffered of hypertensive disease in the II phase during 10 years. Clinically: anxiety-depression and astheno-hypochondriac disorders occurred against the background of the manifest emotional lability. Complaints of strong anxiety, irritability, premature ejaculation. Friction period was 5–10 frictions. Erection was fair. Urologically healthy. The patient rejected out of hands the light filter with the areas letting through red and blue light fluxes. He said that the red irritated him.

All treatment actions in this Example were applied as described in Example 1 for using the apparatus according to the invention. Seven treatment actions were applied. The modes and parameters of the treatment actions are given in Table 5.

After the treatment actions, the emotional condition of the patient normalized, anxiety, irritation and astheno-hypochondriac disorders disappeared. The friction period increased to 60 after the fourth treatment action and to 75–90 after the seventh treatment action so as to be quite suitable for the married couple and the family relations normalized. The individual was then subjected to short-term courses of treatment using the apparatus according to the invention on his request with the regularity of one course every 1.5–4 months on the average.

The treatment actions using the apparatus according to the invention were repeated afterwards on the individual's request.

Therefore the apparatus for treating the emotional condition of an individual makes it possible to act individually upon the left and right hemispheres of the brain simultaneously with different stimuli, namely with light fluxes at wavelengths selected from different wavelength ranges individually for the righthand and lefthand halves of the retinas of the eyes.

We claim:

1. A method for treating an emotional condition of an individual by acting with radiation upon the retinas of the eyes of the individual comprising the steps of

TABLE 5

| Treatment action No. | Day | Light flux from light source 1 (lm) | Distance from the eyes 7 of individual to light source 1 (m) | Duration of treatment action (minutes) | Selected wavelength ranges of the light fluxes 1 10, 11 acting upon: | |
|---|---|---|---|---|---|---|
| | | | | | lefthand halves 16 of the retinas of both eyes 7 ($\times 10^{-7}$ m) | righthand halves 16' of the retinas of both eyes 7 ($\times 10^{-7}$ m) |
| 1 | 2 | 3 | 4 | 5 | 6 | 7 |
| 1 | 1 | 1000 | 1.0 | 4 | 5.10–5.70 | 5.70–5.80 |
| 2 | 2 | 1000 | 1.0 | 6 | 5.20–5.40 | 5.75–5.85 |
| 3 | 4 | 1500 | 1.0 | 1 | 5.75–5.85 | 5.00–5.30 |
| 4 | 4 | 1200 | 1.0 | 4 | 4.90–5.20 | 5.80–6.00 |
| 5 | 5 | 1700 | 1.0 | 1.5 | 5.85–6.20 | 5.00–5.20 |
| 6 | 5 | 1400 | 1.0 | 6 | 5.10–5.30 | 6.20–6.90 |
| 7 | 7 | 1800 | 1.0 | 6 | 5.20–5.40 | 6.40–7.00 |

The treatment actions were applied taking into account the core condition in the structure of the emotional condition of the individual.

EXAMPLE 6

Male individual A, 30. Employed as professor in informatics and computer technology; married, with two childen. Sportsman: plays chess and tennis. Noted a feeling of diffidence and sometimes fear. The individual was proved practically healthy as a result of clinical examinations.

Strong emotional stress as a result of work as operator at a computer center, teaching activities, sports and an active socio-political work during recent three years.

A sensation of fear appeared on several ocasions before competitions, a feeling constraint before the next set so as to result in a loss of game.

Sometimes fatigue, irritation and errors in program compilation occurred after a prolonged work with a large volume of information with a computer.

As a teacher, the patient noted diffidence and a certain perplexity in starting work with a new group of students.

After making the patient familiar with the apparatus according to the invention all treatment actions were applied as described in Example 1. The modes and parameters of the treatment actions are given in Table 6.

(a) forming said radiation into two light fluxes for each eye: a light flux at wavelengths selected from a first wavelength range from $5.85 \times 10^{-7}$ to $7.60 \times 10^{-7}$ m and a light flux at wavelengths selected from a second wavelength range from $3.80 \times 10^{-7}$ to $5.50 \times 10^{-7}$ m, with a boundary separating said light fluxes extending in a plane which is about coincident with a sagittal plane of the eye;

(b) treating a core condition selected from the group consisting of anguish (melancholia), apathy, flabbiness, inhibition, fear, horror, perplexity, hypochondria, derealization and depersonalization by acting simultaneously with the light flux at wavelengths selected from said first wavelength range upon the lefthand halves of the retinas of both eyes and with the light flux at wavelengths selected from the second wavelength range upon the righthand halves of the retinas of both eyes;

(c) treating a condition selected from the group consisting of anxiety, strain, hypomania, malice, suspicion, obsession and irascibility by simultaneously acting with a light flux at wavelengths selected from said second wavelength range upon the lefthand halves of the retinas of both eyes and with a light flux at wavelengths selected from said first wavelength range upon the righthand halves of the retinas of both eyes

TABLE 6

| Treatment action No. | Day | Light flux from light source 1 (lm) | Distance from the eyes 7 of individual to light source 1 (m) | Duration of treatment action (minutes) | Selected wavelength ranges of the light fluxes 10, 11 acting upon: | |
|---|---|---|---|---|---|---|
| | | | | | lefthand halves 16 of the retinas of both eyes 7 ($\times 10^{-7}$ m) | righthand halves 16' of the retinas of both eyes 7 ($\times 10^{-7}$ m) |
| 1 | 1 | 1800 | 1.0 | 3 | 6.70–7.20 | 4.40–4.60 |
| 2 | 4 | 2100 | 1.0 | 2.5 | 6.90–7.60 | 3.80–4.20 |

The condition of the individual normalized, diffidence and fear disappeared.

(d) applying the light fluxes for at least a period until the subjective sensation of a distinct boundary separating the light fluxes disappears; and (e) repeating each previous step at least once.

2. A method for treating an emotional condition of an individual, according to claim 1, wherein:

said light fluxes are formed for both eyes using light filters.

3. A method for treating an emotional condition of an individual according to claim 1 or 2, further comprising the steps of:

(a) forming two auxiliary light fluxes for each eye:

a first auxiliary light flux at wavelengths selected from a third wavelength range from $5.10 \times 10^{-7}$ to $5.60 \times 10^{-7}$ m and a second auxiliary light flux at wavelengths selected from a fourth wavelength range from $5.70 \times 10^{-7}$ to $6.00 \times 10^{-7}$ m, with the boundary separating these light fluxes extending in a plane which is about coincident with the sagittal plane of the eye;

(b) treating the person by acting simultaneously with the auxiliary light flux at wavelengths selected from the third wavelength range upon the righthand halves of the retinas of the eyes, before acting upon said right hand halves of the retinas of the eyes with the light flux at wavelengths selected from the first wavelength range, and acting simultaneously with the auxiliary light flux at wavelengths selected from the fourth wavelength range upon the lefthand halves of the retinas of the eyes before acting upon these (lefthand) halves of the retinas of the eyes with the light flux at wavelengths selected from the second wavelength range;

(c) applying the auxiliary light fluxes for at least a period until the subjective sensation of a distinct boundary separating the light fluxes disappears; and (d) repeating each previous step at least once.

4. A method for treating an emotional condition of an individual by acting with optical radiation upon the retinas of the eyes of the individual comprising the steps of:

(a) forming said radiation in the form of two fluxes for each eye; a light flux at wavelengths selected from a first wavelength range from $5.50 \times 10^{-7}$ to $6.20 \times 10^{-7}$ m and a light flux selected from a second wavelength range from $4.80 \times 10^{-7}$ to $5.40 \times 10^{-7}$ m, with the boundary separating these light fluxes extending in a plane which is about coincident with the sagittal plane of the eye;

(b) treating a core condition selected from the group consisting of anguish (melancholia), apathy, flabbiness, inhibition, fear, horror, perplexity, hypochondria, derealization, and depersonalization, by acting simultaneously with a light flux at wavelengths selected from said first wavelength range upon the lefthand halves of the retinas of both eyes and with a light flux at wavelengths selected from the second wavelength range upon the righthand halves of the retinas of both eyes;

(c) treating a core condition selected from the group consisting of anxiety, strain, hypomania, malice, suspicion, obsession, and irascibility by acting simultaneously with a light flux at wavelengths selected from a sixth wavelength range upon the lefthand halves of the retinas of both eyes and with a light flux at wavelengths selected from said fifth wavelength range upon the righthand halves of the retinas of both eyes;

(d) applying the light fluxes for at least a period until the subjective sensation of a boundary separating the light fluxes disappears; and (e) repeating each previous step at least once.

* * * * *